(12) United States Patent
Fryshman

(10) Patent No.: US 11,045,104 B2
(45) Date of Patent: Jun. 29, 2021

(54) INDUCTION HEATING APPLICATIONS

(71) Applicant: Bernard Fryshman, Brooklyn, NY (US)

(72) Inventor: Bernard Fryshman, Brooklyn, NY (US)

(73) Assignee: Bernard Fryshman, Brooklyn, NY (US)

( * ) Notice: Subject to any disclaimer, the term of this patent is extended or adjusted under 35 U.S.C. 154(b) by 324 days.

(21) Appl. No.: 16/167,101

(22) Filed: Oct. 22, 2018

(65) Prior Publication Data

US 2019/0053716 A1 Feb. 21, 2019

Related U.S. Application Data

(62) Division of application No. 15/491,630, filed on Apr. 19, 2017, now Pat. No. 10,105,069.

(Continued)

(51) Int. Cl.
*H05B 6/12* (2006.01)
*H05B 6/02* (2006.01)
(Continued)

(52) U.S. Cl.
CPC ............... *A61B 5/028* (2013.01); *A61B 5/01* (2013.01); *A61B 5/015* (2013.01); *A61B 5/061* (2013.01);
(Continued)

(58) Field of Classification Search
CPC ........... A61B 90/39; A61B 5/028; A61B 5/01; A61B 5/061; A61B 18/04; A61B 5/015; A61B 2034/2055; A61B 2090/397; A61B 2090/3933; A61B 2090/3954; A61B 2034/2051; A61N 2/02; A61N 1/403; A61F 7/00; A61F 2007/009; A61M 5/44; A61M 5/007
(Continued)

(56) References Cited

U.S. PATENT DOCUMENTS 3,138,698 A 6/1964 Wells et al.
3,221,638 A 12/1965 Wickenberg
(Continued)

FOREIGN PATENT DOCUMENTS

CN 101473789 A 7/2009
CN 205953976 2/2017
(Continued)

OTHER PUBLICATIONS

Non-Final Office Action in U.S. Appl. No. 16/403,978 dated Aug. 20, 2019.
(Continued)

*Primary Examiner* — Quang T Van
(74) *Attorney, Agent, or Firm* — Foley & Lardner LLP

(57) ABSTRACT

A system and method for inductive heating applications includes positioning one or more inductive heating elements in a location, delivering electromagnetic radiation, by a radiation source, to heat at least a portion of the one or more inductive heating elements, and detecting, by a detector, the heat generated by the one or more inductive heating elements. The system and method also include controlling, by a processing unit, a condition based on the detected heat.

18 Claims, 4 Drawing Sheets

Related U.S. Application Data

(60) Provisional application No. 62/325,100, filed on Apr. 20, 2016.

(51) Int. Cl.

| | | |
|---|---|---|
| *H05B 6/10* | (2006.01) |
| *A61B 18/04* | (2006.01) |
| *A61B 5/028* | (2006.01) |
| *A61B 5/01* | (2006.01) |
| *A61F 7/00* | (2006.01) |
| *A61M 5/00* | (2006.01) |
| *A61N 2/02* | (2006.01) |
| *A61N 1/40* | (2006.01) |
| *A61B 5/06* | (2006.01) |
| *A61M 5/44* | (2006.01) |
| *A61B 90/00* | (2016.01) |
| *A61B 34/20* | (2016.01) |

(52) U.S. Cl.
CPC ............. *A61B 18/04* (2013.01); *A61B 90/39* (2016.02); *A61F 7/00* (2013.01); *A61M 5/007* (2013.01); *A61M 5/44* (2013.01); *A61N 1/403* (2013.01); *A61N 2/02* (2013.01); *A61B 2034/2051* (2016.02); *A61B 2034/2055* (2016.02); *A61B 2090/397* (2016.02); *A61B 2090/3933* (2016.02); *A61B 2090/3954* (2016.02); *A61F 2007/009* (2013.01)

(58) Field of Classification Search
USPC ....... 219/622, 621, 618, 625, 626, 600, 665, 219/660, 671, 675; 99/451, DIG. 14, 33, 99/224, 483
See application file for complete search history.

(56) References Cited

U.S. PATENT DOCUMENTS

| | | | |
|---|---|---|---|
| 3,494,722 A | 2/1970 | Gray |
| 3,745,290 A | 7/1973 | Harnden et al. |
| 3,790,735 A | 2/1974 | Peters, Jr. |
| 4,020,310 A | 4/1977 | Souder et al. |
| 4,110,587 A | 8/1978 | Souder et al. |
| 4,418,259 A | 11/1983 | Lewis |
| 4,514,243 A | 4/1985 | Moore et al. |
| 4,766,879 A | 8/1988 | Freese |
| 4,776,386 A | 10/1988 | Meier |
| 4,830,855 A | 5/1989 | Stewart |
| 4,999,467 A | 3/1991 | Iguchi |
| 5,053,593 A | 10/1991 | Iguchi |
| 5,366,764 A | 11/1994 | Sunthankar |
| 5,466,915 A | 11/1995 | Meier et al. |
| 5,508,498 A | 4/1996 | Rheinish et al. |
| 5,611,328 A | 3/1997 | McDermott |
| 5,628,241 A | 5/1997 | Chavanaz et al. |
| 5,665,258 A | 9/1997 | Hsu |
| 5,665,263 A | 9/1997 | Gaspard |
| 5,821,507 A | 10/1998 | Sasaki et al. |
| 5,979,673 A | 11/1999 | Dooley |
| 6,663,615 B1 | 12/2003 | Madou et al. |
| 6,700,183 B2 | 3/2004 | Jiang |
| 6,758,131 B1 | 7/2004 | Joubert |
| 6,864,468 B2 | 3/2005 | Kim et al. |
| 7,170,037 B2 | 1/2007 | Walter |
| 8,803,045 B2 | 8/2014 | Cadima |
| 9,820,690 B1 | 11/2017 | Schwartz et al. |
| 2001/0035406 A1 | 11/2001 | Ryan et al. |
| 2005/0065545 A1 | 3/2005 | Wallace |
| 2006/0102871 A1 | 5/2006 | Wang et al. |
| 2007/0000915 A1 | 1/2007 | Cheng |
| 2007/0023486 A1 | 2/2007 | Matsuura et al. |
| 2009/0065499 A1 | 3/2009 | England |
| 2010/0000980 A1 | 1/2010 | Popescu |
| 2010/0155391 A1 | 6/2010 | Koschberg et al. |
| 2010/0170892 A1 | 7/2010 | Wilson et al. |
| 2011/0245914 A1 | 10/2011 | Santini et al. |
| 2011/0280650 A1 | 11/2011 | Schmitt et al. |
| 2011/0311455 A1 | 12/2011 | Anvari |
| 2012/0041286 A1 | 2/2012 | Goodall et al. |
| 2013/0062527 A1 | 3/2013 | Hyde et al. |
| 2013/0153565 A1 | 6/2013 | Fryshman |
| 2013/0259496 A1* | 10/2013 | Kato .................. G03G 15/0126 399/40 |
| 2014/0042170 A1 | 2/2014 | Correa |
| 2014/0165607 A1 | 6/2014 | Alexander |
| 2014/0217090 A1 | 8/2014 | Fryshman |
| 2014/0238383 A1 | 8/2014 | Armstrong |
| 2015/0126964 A1 | 5/2015 | Martel et al. |
| 2016/0037586 A1 | 2/2016 | Armstrong et al. |
| 2016/0311542 A1 | 10/2016 | Mackin |
| 2016/0370322 A1 | 12/2016 | Hull et al. |
| 2018/0050218 A1 | 2/2018 | Copty |

FOREIGN PATENT DOCUMENTS

| | | |
|---|---|---|
| CN | 107896890 A | 4/2018 |
| JP | 07-275578 A | 10/1995 |
| JP | 2001-250666 A | 9/2001 |
| JP | 2006-172727 A | 6/2006 |
| WO | WO-2010/002751 | 1/2010 |

OTHER PUBLICATIONS

Non-Final Office Action in U.S. Appl. No. 15/876,293, dated Apr. 27, 2020.

* cited by examiner

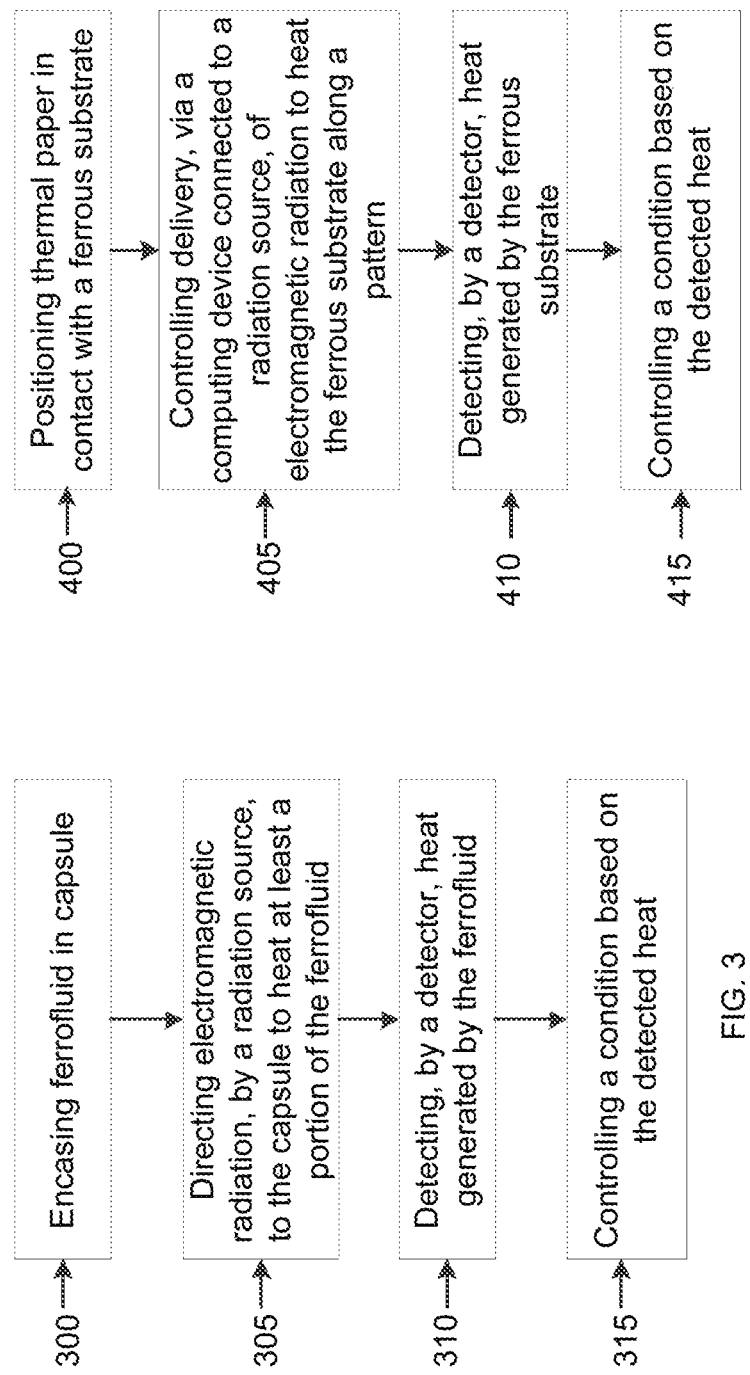

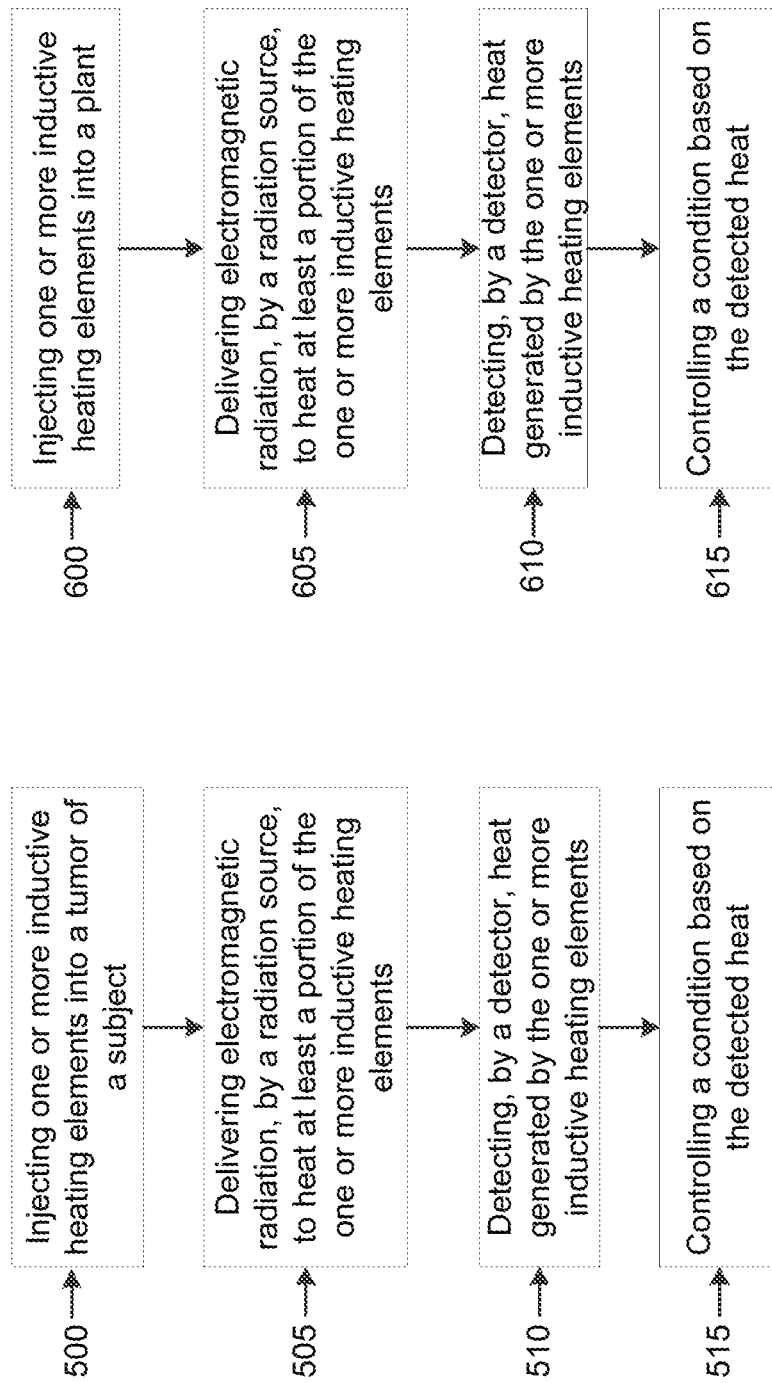

INDUCTION HEATING APPLICATIONS

CROSS REFERENCE TO RELATED APPLICATIONS

This application is a divisional of U.S. patent application Ser. No. 15/491,630, filed Apr. 19, 2017, which claims priority to U.S. Provisional Application 62/325,100, filed on Apr. 20, 2016, the entirety of each are incorporated by reference herein.

BACKGROUND

Induction heating is a form of heating that utilizes an electromagnetic (EM) radiation source to heat a ferrous metal, as opposed to an open flame or heating element. Traditional induction heating is used for food preparation, and involves using a ferrous cooking vessel placed in close proximity to an EM radiation source. Upon activation, the EM radiation source emits EM waves that cause the ferrous cooking vessel to heat up, which in turn heats the contents of the ferrous cooking vessel.

SUMMARY

In accordance with some aspects of the present disclosure, an apparatus is disclosed. The apparatus includes a plurality of inductive heating elements, at least one insulating divider positioned between the plurality of inductive heating elements, and a radiation source configured to deliver electromagnetic radiation to heat at least a portion of the plurality of inductive heating elements to form a pattern to be illuminated on the apparatus.

In accordance with some other aspects of the present disclosure, a method is disclosed. The method includes positioning one or more inductive heating elements in a location, delivering electromagnetic radiation, by a radiation source, to heat at least a portion of the one or more inductive heating elements, and detecting, by a detector, the heat generated by the one or more inductive heating elements. The method also includes controlling, by a processing unit, a condition based on the detected heat.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

FIG. 3 is a flow diagram illustrating a process for using electromagnetic radiation in conjunction with a ferrofluid encased in a capsule in accordance with an illustrative embodiment.

FIG. 4 is a flow diagram illustrating a process for using electromagnetic radiation in conjunction with a thermal paper in contact with a ferrous substrate in accordance with an illustrative embodiment.

FIG. 5 is a flow diagram illustrating a process for using electromagnetic radiation in conjunction with an inductive heating element injected into a tumor of a subject in accordance with an illustrative embodiment.

FIG. 6 is a flow diagram illustrating a process for using electromagnetic radiation in conjunction with an inductive heating element injected into a plant in accordance with an illustrative embodiment.

DETAILED DESCRIPTION

Figure 1:
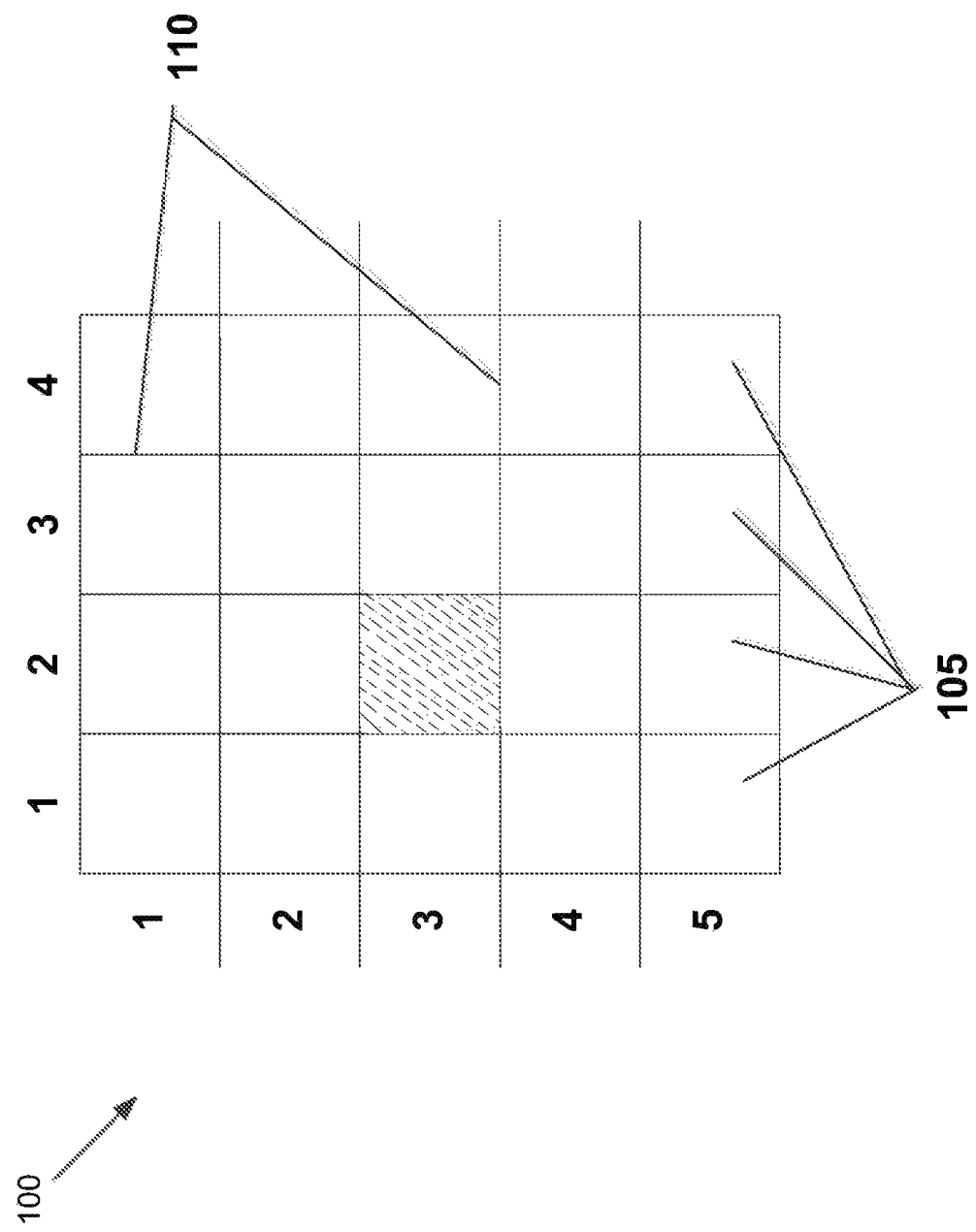
FIG. 1 depicts a sign that is remotely controllable using electromagnetic radiation in accordance with an illustrative embodiment.

Conventional induction cooking involves use of a vessel made of ferrous or similar material, where the vessel receives electromagnetic energy from an EM radiation source. Described herein are a variety of other applications that utilize induction technology to provide targeted heat to a given location. As discussed herein, the use of EM radiation enables the provision of heat at a distance.

Ferrofluid is a name sometimes used to refer to a colloidal liquid that includes ferrous particles which have a diameter of approximately 10 nanometers (nm) or less. In alternative embodiments, the ferrous particles may have a smaller or larger diameter, depending on the application. The ferrous particles can be magnetite, iron, cobalt, nickel, and/or oxides thereof. The ferrous particles may be treated with a surfactant that prevents the particles from bunching up due to magnetic forces. The ferrous particles, when in the presence of an electromagnetic field of the kind used for induction cooking, will heat up, thereby causing the ferrofluid to heat up. Since this and similar colloidal liquids can flow to relatively inaccessible places, such a ferrofluid can be used in a variety of fields where non-invasive testing, monitoring, repair, and/or healing of tissue or other material is called for. Such a ferrofluid can also be used to help destroy unwanted tissue or material.

As one example, for various medical procedures, individuals in the past have been injected with, or asked to swallow, a radioactive fluid such that radioactive emissions can be traced throughout the individual's body using radioactive detectors proximate to the individual. As a result, the patient is subject to potentially harmful radiation. Ferrofluids can be used to replace the use of radioactive fluids for internal tracing/tracking in medical testing and procedures.

In one implementation (e.g., see FIG. 3), a ferrofluid can be encased in a capsule (300) that is swallowed by a patient. The capsule can be made from a plastic or other bio-compatible material. The patient is placed near or into a bank of electromagnetic (EM) radiation sources that are configured to generate EM radiation that targets the swallowed capsule (305). The swallowed capsule increases in temperature as a result of the EM radiation, and the path of the capsule (and ferrofluid therein) can therefore be traced by heat detectors (310, 315). The heat sensors can be mounted directly on a skin surface of the patient, or placed proximate to the patient, depending on the implementation. In an illustrative embodiment, the temperature of the capsule is controlled such that the capsule material does not melt and such that the patient is not burned or otherwise subject to discomfort.

The patient can be a human or a non-human animal. For example, as shown in FIG. 6, Ferrofluids can also be injected into a plant (600) such that progress of the ferrofluid throughout the plant tissue can be monitored (605, 610, 615). Ferrofluids can further be used in industrial processes to detect and/or track the path of a fluid in a closed system. Such tracking will enable the ready detection of obstructions or anomalies in tissue or other closed systems. Ferrofluid tracking will also enable determination of the rate of movement within a closed system, and excessive heat at a given point in the system may signal an obstruction or other problem needing attention. In an alternative embodiment, a bio-compatible ferrofluid may be directly swallowed by or injected into an individual without being encapsulated. In another alternative embodiment, a solid ferrous element may be coated by plastic, etc. and swallowed by an individual for use in tracking/monitoring of the individual. Coating the ferrous element can help to ensure that there is no chemical reaction with or corrosive effect on the body/system into which the ferrous element is introduced.

The use of ferrous material and induction heating allows heating, repair, control, etc. to take place without limitation as to the target area. Where the material to be heated is directly accessible, a ferrous element can be placed directly on or near the material. Upon receipt of EM radiation, the ferrous element will heat up, causing the material on which it is positioned to also heat up. The use of ferrofluids extends this feature by allowing the same technology to be used to provide heat in closed and otherwise inaccessible systems. As an example shown in FIG. 5, a tumor may be located in a living being. A ferrofluid can be injected into the tumor using a standard syringe (500). Upon application of EM radiation to the injected ferrofluid, the ferrofluid can heat up thereby causing the tumor to heat up. The EM radiation can be controlled such that tissue of the tumor is heated to a point where the tissue dies, destroying the tumor in the process (505, 510, 515). Excess heat will pass through surrounding tissue and quickly dissipate without significant discomfort to the person/animal whose tumor is being treated.

In another embodiment, an area to be subjected to heat may be entirely inaccessible. In such instances, a ferrofluid moving through the body or other system can be used in conjunction with highly targeted EM radiation to monitor or treat the area. Specifically, the ferrofluid can be inserted into a closed system that includes the inaccessible area, such as a human body, an animal, a plant, a mechanical system, etc. The inserted ferrofluid will traverse the closed system through the blood stream, digestive system, or other passageways in the system. The targeted EM radiation can be directed to the inaccessible area of the closed system. As the ferrofluid passes through the inaccessible area, it receives the targeted EM radiation and heats up, causing the inaccessible area to receive heat. Such a procedure can be used to treat the inaccessible area with heat, to determine how long it takes for the ferrofluid to travel to the inaccessible area, enhance the effectiveness of medication, etc.

Induction heating can also be used in conjunction with functionalized magnetic nanoparticles which have been used for drug delivery, cell separation, and/or cell stimulation. Having the ability to add heat at a distance significantly expands the efficacy and use of such nanoparticles in medical and other applications. For example, certain chemical reactions take place only in the presence of heat, heat can be used to shed a protective covering of a reactant, and heat can modify a medium for cell growth.

The embodiments described herein can be used anywhere that there is a need or benefit for heat to be present at a distance or through a non-ferrous barrier. As another example, such embodiments can be used in the printing process, which traditionally requires the physical deposition of ink onto paper (or other substrate) or the fusion of carbon onto paper through a laser. In accordance with an illustrative embodiment and as shown in FIG. 4, a thermally sensitive paper (or thermal paper) can be used in conjunction with a ferrous metal substrate. The thermal paper is treated with a chemical that changes color when exposed to heat. As a non-limiting example, the chemical used to treat the paper can be a solid-state mixture of a dye and a suitable matrix, such as a combination of a fluoran leuco dye. Upon heating of the matrix to a temperature above its melting point, the dye reacts with the acid, changes color, and then remains as the changed color upon cooling of the matrix back into a solid state.

Such a thermal paper can be used in conjunction with a ferrous substrate to print from a distance using induction heating technology. Specifically, the thermal paper can be placed in contact with or near the ferrous substrate (400). Targeted EM radiation can be applied from a distance to various portions of the ferrous substrate, which causes the ferrous substrate and hence the thermal paper to heat up (405, 410). The heated portions of the thermal paper change color and this process can be used to impose letters, numbers, images, etc. onto the thermal paper (415). In one implementation, the ferrous substrate can be divided into a plurality of small, individually targetable areas (spatially similar to pixels in a liquid crystal display), and a computing device can be used to control targeting of the EM radiation to form a pattern, image, text, etc. on the substrate such that the pattern, image, text, etc. is imposed onto the thermal paper. The computing device can include instructions stored on a memory and executable by a processor. Various areas of the thermal paper can be heated simultaneously to form the image onto the paper. Alternatively, the targeted EM radiation can be used to iteratively form the image one area at a time.

In another illustrative embodiment, the thermal paper can be configured such that heating at different temperatures will result in the generation of different colors. In such an implementation, color images, patterns, text, etc. can be imposed on the thermal paper. Such a multicolor thermal paper can be generated using multi-layer coatings in which each coating layer results in a different color activated at a different temperature. The different temperatures can be achieved in different areas by selectively controlling the magnitude, duration, and location of the EM radiation onto the ferrous substrate proximate to the multicolor thermal paper. As a result of these embodiments, it will be possible to print at a distance without the need for physical deposition of an ink or fusion of carbon.

In another embodiment, induction heating can be used to power a sign in an area where there is no source of electrical power. The sign can, for example include a plurality of ferrous elements in a grid-like or other pattern and the ferrous elements can be separated from one another by non-ferrous insulating dividers. Targeted EM radiation can be used to heat up specific ferrous elements of the sign in the form of a pattern, image, text, etc. The heat generated by the ferrous elements can cause the ferrous elements to become visible in a dark environment such that the pattern, image, text, etc. on the sign appears to be lit up. Alternatively, the heated pattern may cause a visible reaction of another material incorporated into the sign, again causing the heated areas to become visible in a dark environment.

FIG. 1 depicts such a sign 100 in accordance with an illustrative embodiment. The sign 100 includes a plurality of squares of ferrous elements 105 which are separated from one another by insulating barriers 110. The ferrous elements 105 of the sign 100 are arranged in a grid-like pattern and can be controlled by targeting desired portions of the grid. As depicted in FIG. 1, the ferrous element at location (3, 2) is being targeted with EM radiation and is therefore visible on the sign. A large sign can be composed of hundreds or thousands of such targetable ferrous elements in a grid-like or other pattern.

Figure 2:
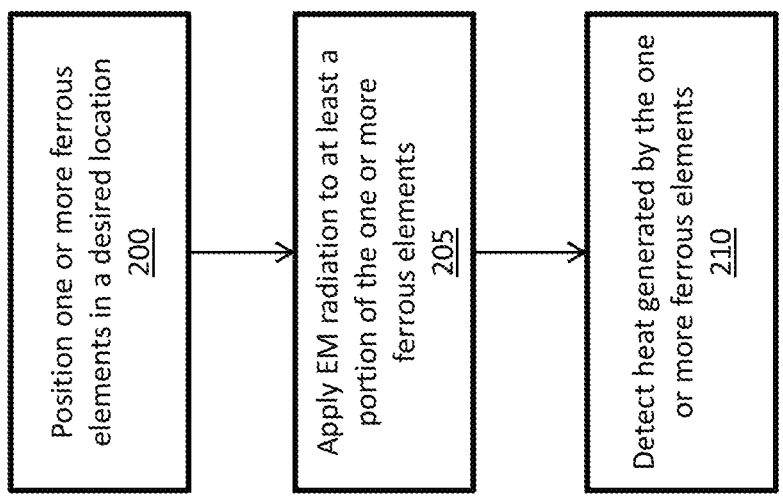
FIG. 2 is a flow diagram illustrating a process for remotely heating objects in accordance with an illustrative embodiment.

FIG. 2 is a flow diagram illustrating a process for remotely heating objects in accordance with an illustrative embodiment. In an operation 200, one or more ferrous elements are positioned in a desired location. The one or more ferrous elements can refer to ferrous particles in a ferrofluid that is to be swallowed by or injected into a patient, ferrous elements arranged in a sign, a ferrous plate used for remote printing, etc.

In an operation 205, EM radiation is applied to at least a portion of the one or more ferrous elements. The EM radiation can be applied by any type of EM radiation source known to those of skill in the art. In an illustrative embodiment, the EM radiation is applied in a targeted manner such that only a portion of the one or more ferrous elements are heated. In such an embodiment, the EM radiation can be applied in a particular pattern such that a shape, image, text, etc. is formed as a result of the heated pattern. A computing device can be used to determine the pattern and to apply the EM radiation in the targeted pattern. In an alternative embodiment, the one or more ferrous elements may be completely bathed in EM radiation such that all of the ferrous elements are caused to heat up.

In an operation 210, heat that is generated by the one or more ferrous elements is detected. For example, in the context of tracing materials in a closed system, detectors can be used to determine the amount of time it takes for the ferrous elements to travel a certain distance, whether there are impassable blockages in certain areas, etc. In alternative embodiments such as activation of thermal paper, the operation 210 may not be performed as there is no need to detect the heat in such implementations.

In an illustrative embodiment, control of the heating elements described herein can be implemented at least in part as computer-readable instructions stored on a computer-readable medium, such as a computer memory or storage device. Upon execution of the computer-readable instructions by a processor, the computer-readable instructions can cause the computing device to perform the operations to heat materials in a desired fashion.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments.

What is claimed is:

1. An apparatus comprising:
    a plurality of inductive heating elements arranged in a first pattern;
    a non-ferrous divider positioned between the plurality of inductive heating elements; and
    a radiation source configured to deliver electromagnetic radiation to heat at least a portion of the plurality of inductive heating elements to form a second pattern within the first pattern to be illuminated on the apparatus.

2. The apparatus of claim 1, wherein the plurality of inductive heating elements are arranged in a grid on the apparatus.

3. The apparatus of claim 1, wherein the at least a portion of the plurality of inductive heating elements are configured to be lit up from the heat to illuminate the second pattern.

4. The apparatus of claim 1, wherein the at least a portion of the plurality of inductive heating elements are configured to heat another material positioned proximate to the at least a portion of the plurality of inductive heating elements to illuminate the second pattern.

5. The apparatus of claim 1, wherein the non-ferrous divider is a thermally insulating divider.

6. The apparatus of claim 1, wherein each of the plurality of inductive heating elements is separated from another one of the plurality of inductive heating elements by the non-ferrous divider.

7. The apparatus of claim 1, further comprising a computing device configured to determine the second pattern.

8. The apparatus of claim 7, wherein the computing device is configured to apply the electromagnetic radiation, via the radiation source, to the plurality of inductive heating elements whose locations correspond to the second pattern.

9. The apparatus of claim 1, wherein the second pattern comprises at least one of an image and text.

10. The apparatus of claim 1, wherein the apparatus comprises a sign to be illuminated without electric power.

11. A method comprising:
    delivering electromagnetic radiation from an electromagnetic radiation source to illuminate a second pattern on an apparatus,
    wherein the apparatus comprises a plurality of inductive heating elements arranged in a first pattern and a non-ferrous divider positioned between the plurality of inductive heating elements;
    wherein the electromagnetic radiation is configured to heat at least a portion of the plurality of inductive heating elements; and
    wherein heating the at least a portion of the plurality of inductive heating elements forms the second pattern within the first pattern that is illuminated on the apparatus.

12. The method of claim 11, wherein the plurality of inductive heating elements are arranged in a grid on the apparatus.

13. The method of claim 12, wherein each of the plurality of inductive heating elements is separated from an adjacent one of the plurality of inductive heating elements by the non-ferrous divider.

14. The method of claim 11, further comprising heating another material positioned proximate to the at least a portion of the plurality of inductive heating elements for forming the second pattern that is illuminated on the apparatus.

15. The method of claim 11, further comprising:
    determining, by a computing device, the second pattern to be illuminated on the apparatus; and
    delivering, by the computing device, the electromagnetic radiation via the electromagnetic radiation source to the plurality of inductive heating elements whose locations correspond to the second pattern.

16. The method of claim 11, wherein the at least a portion of the plurality of inductive heating elements are configured to be lit up from the heat for illuminating the second pattern on the apparatus.

17. The method of claim 11, wherein the second pattern comprises at least one of an image and text.

18. The method of claim 11, wherein the apparatus comprises a sign to be illuminated without electric power.

\* \* \* \* \*